US011915418B2

(12) United States Patent
Matsutani

(10) Patent No.: US 11,915,418 B2
(45) Date of Patent: Feb. 27, 2024

(54) IMAGE PROCESSING APPARATUS AND IMAGE PROCESSING METHOD

(71) Applicant: Konica Minolta, Inc., Tokyo (JP)

(72) Inventor: Noritsugu Matsutani, Musashino (JP)

(73) Assignee: KONICA MINOLTA, INC., Tokyo (JP)

( * ) Notice: Subject to any disclaimer, the term of this patent is extended or adjusted under 35 U.S.C. 154(b) by 319 days.

(21) Appl. No.: 17/340,608

(22) Filed: Jun. 7, 2021

(65) Prior Publication Data
US 2021/0390691 A1 Dec. 16, 2021

(30) Foreign Application Priority Data

Jun. 11, 2020 (JP) .................................. 2020-101305

(51) Int. Cl.
*G06K 9/00* (2022.01)
*A61B 6/12* (2006.01)
*G06T 7/00* (2017.01)

(52) U.S. Cl.
CPC .............. *G06T 7/0012* (2013.01); *A61B 6/12* (2013.01); *A61B 6/469* (2013.01); *A61B 6/50* (2013.01); *G06T 2207/10116* (2013.01); *G06T 2207/30061* (2013.01)

(58) Field of Classification Search
CPC .............. G06K 9/00; G06T 11/60; G06T 7/00
USPC ...... 382/100, 103, 10–6, 107, 128–132, 154, 382/162, 168, 173, 181, 199, 224, 219, 382/254, 274–276, 286–292, 312; 378/62, 28, 4
See application file for complete search history.

(56) References Cited

U.S. PATENT DOCUMENTS

| 9,901,317 | B2* | 2/2018 | Shimamura | G06T 7/62 |
| 2014/0254762 | A1* | 9/2014 | Yamato | A61B 6/541 |
| | | | | 378/62 |
| 2018/0018772 | A1* | 1/2018 | Fujiwara | G06T 11/60 |
| 2018/0268555 | A1* | 9/2018 | Muraoka | G06T 7/0016 |
| 2018/0368797 | A1* | 12/2018 | Kuwata | A61B 6/5217 |
| 2019/0090835 | A1* | 3/2019 | Matsutani | A61B 6/504 |

FOREIGN PATENT DOCUMENTS

| JP | 2006-130129 A | 5/2006 |
| JP | 2012-011120 A | 1/2012 |

* cited by examiner

*Primary Examiner* — Seyed H Azarian
(74) *Attorney, Agent, or Firm* — LUCAS & MERCANTI, LLP

(57) ABSTRACT

Provided is an image processing device including a hardware processor. The hardware processor: obtains a static image and a dynamic image of a same subject by radiographic imaging; detects, on the static image, a first analysis target area; detects, on the dynamic image, a second analysis target area corresponding to the first analysis target area; analyzes the second analysis target area of the dynamic image to generate a functional information representative from change caused by biological motion; deforms and positions the second analysis target area so that the second analysis target area corresponds to the first analysis target area; overlays the functional information representative of the deformed and positioned second analysis target area on the static image.

15 Claims, 8 Drawing Sheets

ABNORMAL SITE (LUNG MOTION AMOUNT)

LUNG MOTION AMOUNT

ABNORMAL SITE (LUNG MOTION AMOUNT)

THORAX WIDTH

THORAX WIDTH

LUNG FIELD AREA

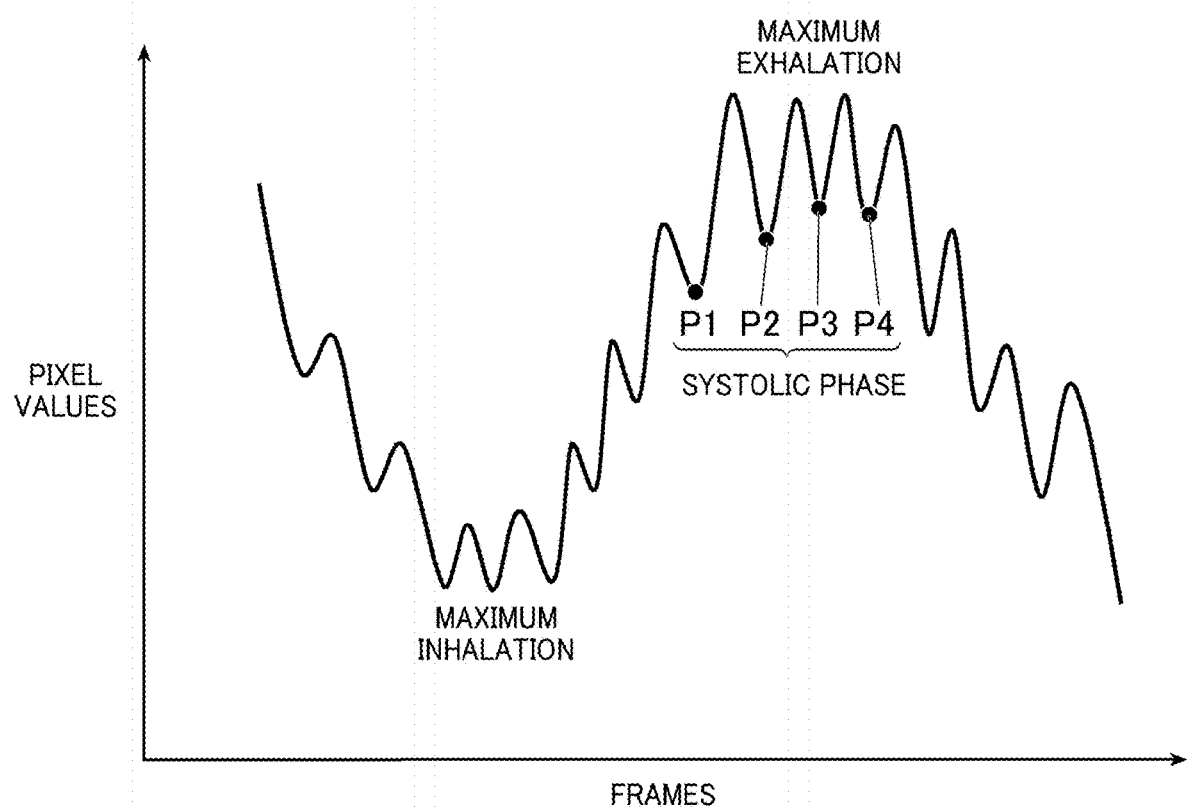

IMAGE PROCESSING APPARATUS AND IMAGE PROCESSING METHOD

CROSS-REFERENCE TO RELATED APPLICATIONS

The entire disclosure of Japanese Patent Application No. 2020-101305 filed on Jun. 11, 2020 is incorporated herein by reference in its entirety.

BACKGROUND

Technological Field

The present invention relates to an image processing apparatus and an image processing method.

Description of the Related Art

A static image obtained in a conventional radiological imaging examination does not contain information on motions that give functional information, and allows evaluation of morphological information only. On contrary, a dynamic image obtained by radiological imaging of dynamics of a living body enables observations of lung motion along with respiration, blood flow motion, and the like, and are expected to be beneficially used for diagnosis of diseases.

However, a dynamic image, which is constituted of multiple frame images, contains a lot of information compared to a static image, and it takes time to extract useful information from a dynamic image.

To deal with such a problem, there is disclosed a technique for an X-ray diagnostic device in which X-rays are emitted to a subject and X-rays transmitted through the subject are detected so as to display an X-ray moving image, where images of high importance are selected from an X-ray moving image and the selected images are listed as thumbnails (see JP2012011120A).

There is disclosed another technique for an X-ray diagnostic device that records multiple X-ray transmission images obtained by X-ray imaging of multiple times in a predetermined period of time as continuous images, where a region of interest in a series of images is set based on pixel values on X-ray transmission images and the X-ray transmission images of the set region of interest are continuously displayed (see JP2006130129A).

SUMMARY

However, even in the techniques of JP2012011120A and JP2006130129A, multiple images are selected from a dynamic image, and therefore it takes some time to interpret the images. As described above, it takes more time to read information from a dynamic image than from a static image, requiring doctors to take more time to give a diagnosis.

The present invention has been conceived in view of the above problems in the prior art, and has an object of saving doctors time for diagnosis.

To achieve at least one of the abovementioned objects, an image processing apparatus reflecting one aspect of the present invention includes a hardware processor,
wherein the hardware processor:
obtains a static image and a dynamic image of a same subject by radiographic imaging;
detects, on the static image, a first analysis target area;
detects, on the dynamic image, a second analysis target area corresponding to the first analysis target area;
analyzes the second analysis target area of the dynamic image to generate a functional information representative from change caused by biological motion;
deforms and positions the second analysis target area so that the second analysis target area corresponds to the first analysis target area;
overlays the functional information representative of the deformed and positioned second analysis target area on the static image.

To achieve at least one of the abovementioned objects, an image processing method reflecting another aspect of the present invention includes:
obtaining a static image and a dynamic image of a same subject by radiographic imaging;
detecting, on the static image, a first analysis target area;
detecting, on the dynamic image, a second analysis target area corresponding to the first analysis target area;
analyzing the second analysis target area of the dynamic image to generate a functional information representative from change caused by biological motion;
deforming and positioning the second analysis target area so that the second analysis target area corresponds to the first analysis target area;
overlaying the functional information representative of the deformed and positioned second analysis target area on the static image.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention, wherein:

FIG. 11 is an explanatory drawing showing a method of creating a static image from part of a dynamic image.

DETAILED DESCRIPTION OF THE EMBODIMENTS

Hereinafter, one or more embodiments of the present invention are described with reference to the drawings. However, the scope of the invention is not limited to the disclosed embodiments.

[Configuration of Imaging System]

Figure 1:
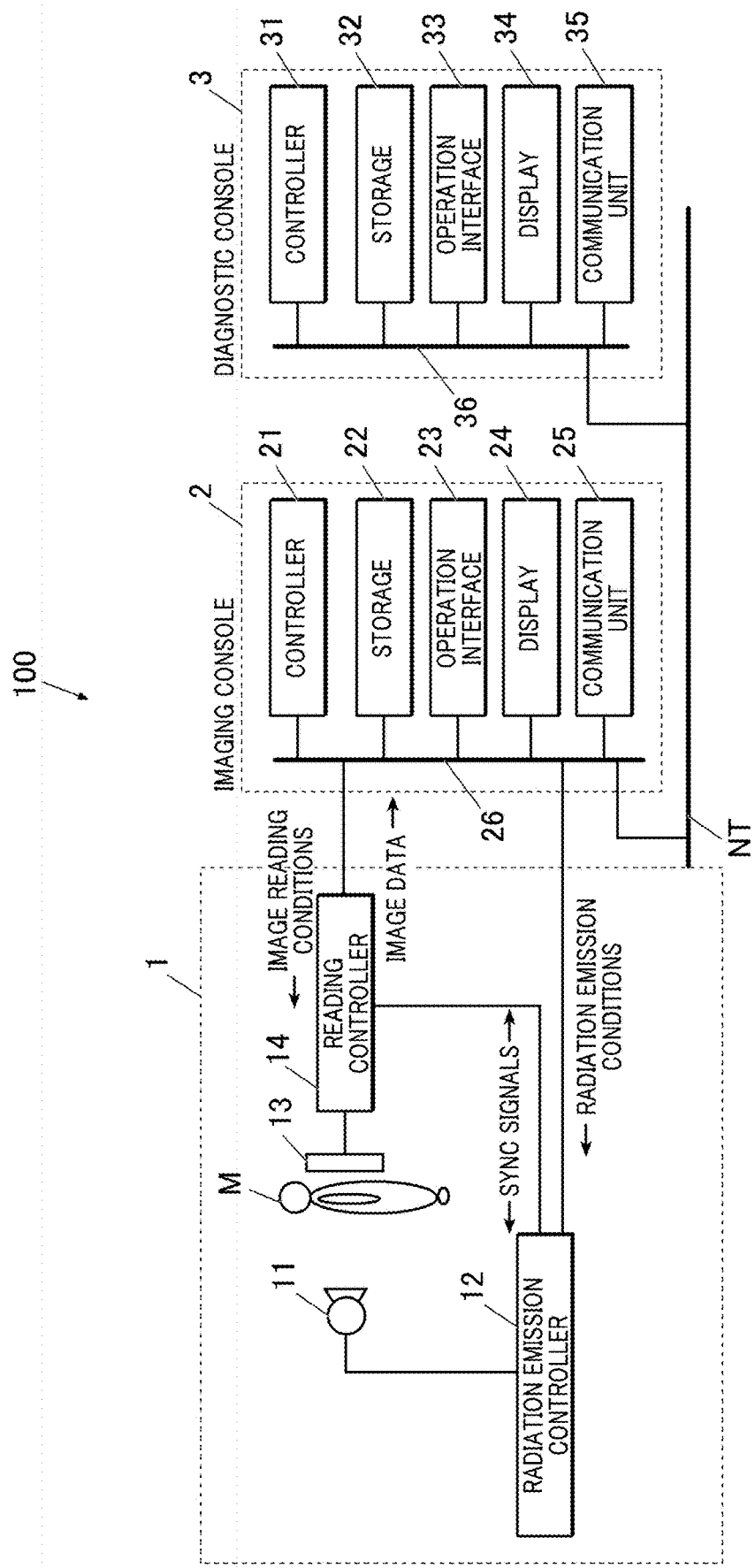
FIG. 1 shows an overall configuration of an imaging system according to an embodiment of the present invention.

FIG. 1 shows an overall configuration of an imaging system 100 according to this embodiment.

As shown in FIG. 1, the imaging system 100 includes: an imaging device 1; an imaging console 2 connected with the imaging device 1 via a communication cable or the like; and a diagnostic console 3 connected with the imaging console 2 via a communication network NT, such as a LAN (local area network). The components of the imaging system 100 are in conformity with DICOM (Digital Image and Communications in Medicine) standard and communicate with one another in conformity with DICOM.

[Configuration of Imaging Device]

The imaging device 1 is an imaging device that images a cyclic dynamic state. The cyclic dynamic state includes: change in shape of the lungs by expansion and contraction of the lungs with breathing; and pulsation of the heart. Dynamic imaging is performed by repeatedly emitting pulsed radiation, such as X-rays, to a subject M at predetermined time intervals (pulse emission) or continuously emitting radiation without a break to a subject M at a low dose rate (continuous emission), thereby obtaining a plurality of images showing the dynamic state of the subject M. A series of images obtained by dynamic imaging is called a dynamic image Images constituting a dynamic image are called frame images. In the embodiment below, dynamic imaging of the frontal chest by pulse emission is described as an example. The imaging device 1 can also take a static image.

A radiation source 11 is disposed to face a radiation detector 13 having a subject M in between, and emits radiation (X-rays) to the subject M under the control of a radiation emission controller 12.

The radiation emission controller 12 is connected with the imaging console 2, and controls the radiation source 11 on the basis of radiation emission conditions input from the imaging console 2 so as to perform radiation imaging. The radiation emission conditions input from the imaging console 2 include a pulse rate, a pulse width, a pulse interval, the number of frames (frame images) to be taken by one imaging, a value of current of an X-ray tube, a value of voltage of the X-ray tube, and a type of added filter. The pulse rate is the number of times radiation is emitted per second, and matches the frame rate described below. The pulse width is a period of time for one radiation emission. The pulse interval is a period of time from the start of one radiation emission to the start of the next radiation emission, and matches the frame interval described below.

The radiation detector 13 is constituted of a semiconductor image sensor such as a flat panel detector (FPD). The FPD is constituted of detection elements (pixels) arranged at predetermined points on a substrate, such as a glass substrate, in a matrix. The detection elements detect radiation (intensity of radiation) that has been emitted from the radiation source 11 and passed through at least a subject M, convert the detected radiation into electric signals, and accumulate the electric signals therein. The pixels are provided with switches, such as TFTs (Thin Film Transistors). There are an indirect conversion type FPD that converts X-rays into electric signals with photoelectric conversion element(s) via scintillator(s) and a direct conversion type FPD that directly converts X-rays into electric signals. Either of them can be used.

The radiation detector 13 is disposed to face the radiation source 11 having a subject M in between.

A reading controller 14 is connected with the imaging console 2. The reading controller 14 controls the switches of the pixels of the radiation detector 13 on the basis of image reading conditions input from the imaging console 2 to switch the pixels to read the electric signals accumulated in the pixels, thereby reading the electric signals accumulated in the radiation detector 13 and obtaining image data. The image data is each frame image of a dynamic image or a static image. In each frame image of a dynamic image and each pixel of a static image, existence of a structure decreases an amount of radiation reaching the radiation detector 13 and decreases pixel values (density values). For example, in the lung field area of the chest image containing ribs, pulmonary vessels, tumors, and the like, density values are lower than in the background lung field area. The reading controller 14 outputs the obtained dynamic or static image to the imaging console 2. The image reading conditions include a frame rate, a frame interval, a pixel size, and an image size (matrix size). The frame rate is the number of frame images to be obtained per second, and matches the pulse rate described above. The frame interval is a period of time from the start of one frame image obtaining action to the start of the next frame image obtaining action, and matches the pulse interval described above.

The radiation emission controller 12 and the reading controller 14 are connected to each other, and exchange sync signals so as to synchronize radiation emission actions with image reading actions.

[Configuration of Imaging Console 2]

The imaging console 2 outputs the radiation emission conditions and the image reading conditions to the imaging device 1 so as to control the radiation imaging and the radiation image reading actions performed by the imaging device 1, and also displays a dynamic image or static image obtained by the imaging device 1 so that a radiographer, such as a radiologist, can check if positioning has no problem, and also can determine if the dynamic image is suitable for diagnosis.

The imaging console 2 includes, as shown in FIG. 1, a controller 21, a storage 22, an operation interface 23, a display 24 and a communication unit 25. These components are connected with one another via a bus 26.

The controller 21 includes a CPU (Central Processing Unit) and a RAM (Random Access Memory). The CPU of the controller 21 reads a system program and various process programs stored in the storage 22 in response to operation on the operation interface 23, opens the read programs in the RAM, and performs various processes, such as an imaging control process (see FIG. 3), in accordance with the opened programs, thereby performing concentrated control of actions of the components of the imaging console 2 and the radiation emission actions and the reading actions of the imaging device 1.

The storage 22 is constituted of a non-volatile semiconductor memory, a hard disk, or the like. The storage 22 stores therein various programs to be executed by the controller 21, parameters necessary to perform processes of the programs, data, such as process results, and the like. For example, the storage 22 stores therein a program for the imaging control process. The storage 22 also stores therein the radiation emission conditions and the image reading conditions for respective regions to be imaged. The programs are stored in the form of a computer readable program code(s), and the controller 21 executes operations in accordance with the program code.

The operation interface 23, which includes a keyboard with cursor keys, letter and number input keys, various function keys, etc. and a pointing device such as a mouse, outputs operation signals input through keyboard operations or mouse operations to the controller 21. The operation interface 23 may have a touchscreen on the display screen of the display 24. In that case, the operation interface 23 outputs command signals input via the touchscreen to the controller 21.

The display 24 is constituted of a monitor such as an LCD (Liquid Crystal Display), and displays thereon commands input from the operation interface 23, data and the like in accordance with commands of display signals input from the controller 21.

The communication unit 25 includes a LAN adapter, a modem and a TA (Terminal Adapter), and controls data exchange with devices connected to the communication network NT.

[Configuration of Diagnostic Console 3]

The diagnostic control 3 is an image processing apparatus that obtains a dynamic image or a static image from the imaging console 2, analyzes the image, and displays the obtained image and/or the analysis result of the image to help a doctor(s) make a diagnosis.

The diagnostic console 3 includes, as shown in FIG. 1, a controller 31 (hardware processor), a storage 32, an operation interface 33, a display 34, and a communication unit 35. These components are connected with one another via a bus 36.

The controller 31 includes a CPU and a RAM. The CPU of the controller 31 reads a system program and various process programs stored in the storage 32 in response to operation on the operation interface 33, opens the read programs in the RAM, and performs various processes such as the functional information representative addition process (see FIG. 4), in accordance with the opened programs, thereby performing central control of actions of the components of the diagnostic console 3.

The storage 32 is constituted of a non-volatile semiconductor memory, a hard disk or the like. The storage 32 stores therein various programs, including a program for the functional information representative addition process, to be executed by the controller 31, parameters necessary to perform processes of the programs, data such as process results, and the like. The programs are stored in a form of a computer readable program code(s), and the controller 31 executes operations in accordance with the program code.

The storage 32 stores dynamic or static images associated with patient information (patient ID, patient name, height, weight, age, sex, etc.) and examination information (examination ID, examination date, imaged region, etc.).

The operation interface 33, which includes a keyboard with cursor keys, letter and number input keys, various function keys, etc. and a pointing device such as a mouse, outputs command signals input through keyboard operations or mouse operations to the controller 31. The operation interface 33 may have a touchscreen on the display screen of the display 34. In that case, the operation interface 33 outputs command signals input via the touchscreen to the controller 31.

The display 34 is constituted of a monitor such as an LCD, and performs various types of display in accordance with commands of display signals input from the controller 31.

The communication unit 35 includes a LAN adapter, a modem and a TA, and controls data exchange with devices connected to the communication network NT.

The controller 31 obtains a static image and a dynamic image obtained by radiological imaging of the same subject M. The controller 31 functions as an obtaining means.

The controller 31 detects a first analysis target area on the static image. The controller 31 functions as a first detecting means.

The controller 31 detects a second analysis target area corresponding to the first analysis target area on a dynamic image. The controller 31 functions as a second detecting means.

The analysis target areas (first analysis target area, second analysis target area) are specified in advance for each function (functional information representative). The analysis target areas for each function (functional information) are stored in the storage 32. For example, the lung field is detected on a frontal chest image by which ventilation and blood flow are analyzed.

The controller 31 analyzes a dynamic image in the second analysis target area, and generates a "functional information representative" from change caused by biological motion. The controller 31 functions as a generating means.

Specifically, the controller 31 analyses the second analysis target area in each frame image of a dynamic image and generates functional information for each frame image. The functional information is information obtained from change caused by biological motion. The controller 31 generates the functional information representative as information on the representative function in a dynamic image based on the functional information generated for each frame image.

The functional information representative includes information indicating ventilation, blood flow, a ventilation and blood flow balance, a lung motion amount, lung movement directions, and the like.

The functional information representative also includes information indicating an abnormal site.

The functional information representative also includes information concerning a measurement of thorax width, diaphragm motion amount, respiratory tract diameter, heart width, lung field area, respiratory tract area, heart area, and the like.

The functional information (functional information representative) is divided into an image group and a measurement group.

The functional information (functional information representative) included in the image group is, for example, ventilation, blood flow, a ventilation and blood flow balance, a lung motion amount, lung movement directions, an abnormal site, and the like.

Ventilation is presented by change in pixel values of a low frequency synchronized with respiration. The functional information indicating ventilation is information on the size of change in flows of exhalation and inhalation by respiration in each position (pixel) given as pixel values. The functional information (functional information representative) indicating ventilation is displayed as an image colored according to such pixel values.

Blood flow is presented by change in pixel values of a high frequency synchronized with heartbeat. The functional information indicating blood flow is information on the size of change in blood flow in each position (pixel) given as pixel values. The functional information (functional information representative) indicating blood flow is displayed as an image colored according to such pixel values.

A ventilation and blood flow balance is a ratio between ventilation and blood flow. The functional information indicating a ventilation and blood flow balance is information on the ratio between ventilation and blood flow in each position (pixel) given as pixel values. The functional information (functional information representative) indicating a ventilation and blood flow balance is displayed as an image colored according to such pixel values.

A lung motion amount is an amount of movement at each position of the lungs along with respiration, which is obtained, for example, by an amount of movement at a required position calculated by an optical flow process. The functional information indicating a lung motion amount is information on an amount of movement in each position (pixel) given as pixel values. The functional information (functional information representative) indicating a lung motion amount is displayed as an image colored according to such pixel values.

Lung movement directions (angle) are information on directions of movement of the lungs along with respiration, which is obtained, for example, by movement directions at positions calculated by an optical flow process. The functional information indicating lung movement directions is information on movement directions at positions associated with respective positions (pixels). The functional information (functional information representative) indicating directions of movement is displayed as an image colored according to the directions of movement at respective positions (pixels).

An abnormal site is a site with an abnormality detected from results of analysis of ventilation, blood flow, ventilation and blood flow balance, lung motion amount, lung movement directions, or the like. For example, a threshold value of a movement is 1 cm, a site where the movement is smaller than 1 cm is an abnormal site. The functional information representative indicating an abnormal site is displayed on an image on which pixels of a part corresponding to an abnormal site are represented by a color distinguished from the rest of the image.

An abnormal site is detected on each image that corresponds to each frame image of a dynamic image and that has signal values of the functional information indicating ventilation, blood flow, a ventilation and blood flow balance, a lung motion amount, lung movement directions, or the like given as pixel values. Which function is used in detection of an abnormal site may be determined by a user or preset in advance.

The functional information (functional information representative) included in the measurement group is, for example, a thorax width, a diaphragm motion amount, a respiratory tract diameter, a heart width, a lung field area, a respiratory tract area, and a heart area.

The functional information representative indicating the thorax width, diaphragm motion amount, respiratory tract diameter, or heart width includes the minimum value and the maximum value (or change amount) of measured results concerning each part. The functional information representative indicating the thorax width, diaphragm motion amount, respiratory tract diameter, or heart width may include lines, dots, or arrows indicating the part of the measurement target.

The functional information representative indicating the lung field area, respiratory tract area, or heart area includes the minimum value and the maximum value (or change amount) of measured results concerning each part. The functional information representative indicating the lung field area, respiratory tract area, or heart area may include contours indicating the area corresponding to the measured area.

The controller 31 generates the functional information representative from a frame image (singular point) where change caused by biological motion is the maximum among multiple frame images of a dynamic image. The singular point is a representative frame image corresponding to a representative moment in dynamics among frame images of a dynamic image.

For example, for ventilation or blood flow, the controller 31 specifies a frame image where the average signal value of ventilation or blood flow in the lung field as a singular point, and specifies the functional information (visualized information indicating signal values of ventilation or blood flow) at the singular point as the functional information representative.

For a thorax width or lung field area, the controller 31 specifies a frame image where the thorax width or lung field area is the maximum and a frame image where the thorax width or lung field area is the minimum as singular points, and generates the functional information representative from the functional information (maximum and minimum values) at the singular points.

The controller 31 generates a single representative image by image processing of multiple images with pixel values indicating change caused by biological motion corresponding to each of multiple frame images of a dynamic image.

The image processing may be maximum intensity projection processing, minimum intensity projection processing, or peak-to-peak processing, for example.

In the maximum intensity projection processing, the maximum signal values for respective pixels (positions) along time are calculated from a functional information image (an image with pixel values of signal values indicating ventilation, blood flow, etc.) corresponding to each frame image and are used as pixel values.

In the minimum intensity projection processing, the minimum signal values for respective pixels (positions) along time are calculated from a functional information image (an image with pixel values of signal values indicating ventilation, blood flow, etc.) corresponding to each frame image and are used as pixel values.

In the peak-to-peak processing, the maximum and minimum signal values for respective pixels (positions) along time are calculated from a functional information image (an image with pixel values of signal values indicating ventilation, blood flow, etc.) corresponding to each frame image, and differences between the maximum and minimum values are used as pixel values.

The controller 31 deforms and positions the second analysis target area so that the second analysis target area corresponds to the first analysis target area. The controller 31 functions as a position adjusting means.

The controller 31 overlays on the static image the functional information representative in the second analysis target area which has undergone the deformation and positioning. The controller 31 functions as an overlaying means.

The controller 31 displays, on the display 34, the static image on which the functional information representative is overlaid. The controller 31 functions as a display controlling means.

[Outline of Invention]

Figure 2:
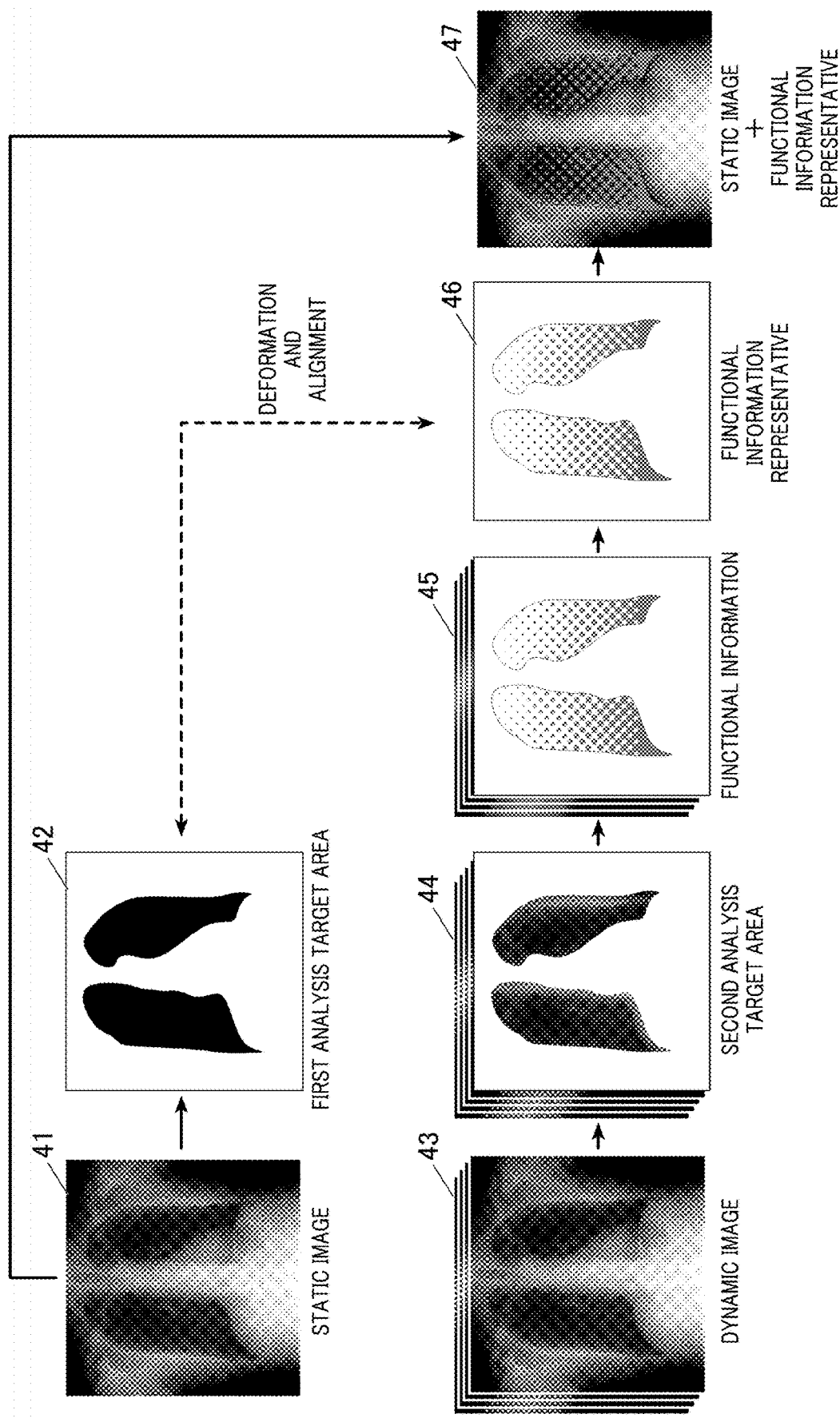
FIG. 2 shows an outline of the present invention.

FIG. 2 shows an outline of the present invention.

The first analysis target area 42 is detected on the static image 41, and the second analysis target area 44 corresponding to the first analysis target area 42 is detected on each frame image of the dynamic image 43. The order of detection of the first analysis target area 42 and the second analysis target area 44 is not limited, and whichever area may be detected first.

The functional information 45 is generated for the second analysis target area 44 on each frame image, and the functional information representative 46 representing the dynamic image 43 is generated from the functional information 45 of each frame image.

The second analysis target area 44 including the functional information representative 46 is deformed and positioned so that the second analysis target area 44 corresponds to the first analysis target area 42.

The deformed and positioned functional information representative 46 is overlaid on the static image 41, and a static image 47 with the functional information representative is generated.

The functional information 45 (functional information representative 46) obtained from the dynamic image 43 may be read on the static image 47 with the functional information representative even though the static image 47 is a single image.

[Operation of Imaging System]

Next, the operation of the imaging system 100 is described.

(Actions of Imaging Device and Imaging Console)

First, imaging actions by the imaging device 1 and the imaging console 2 are described.

Figure 3:
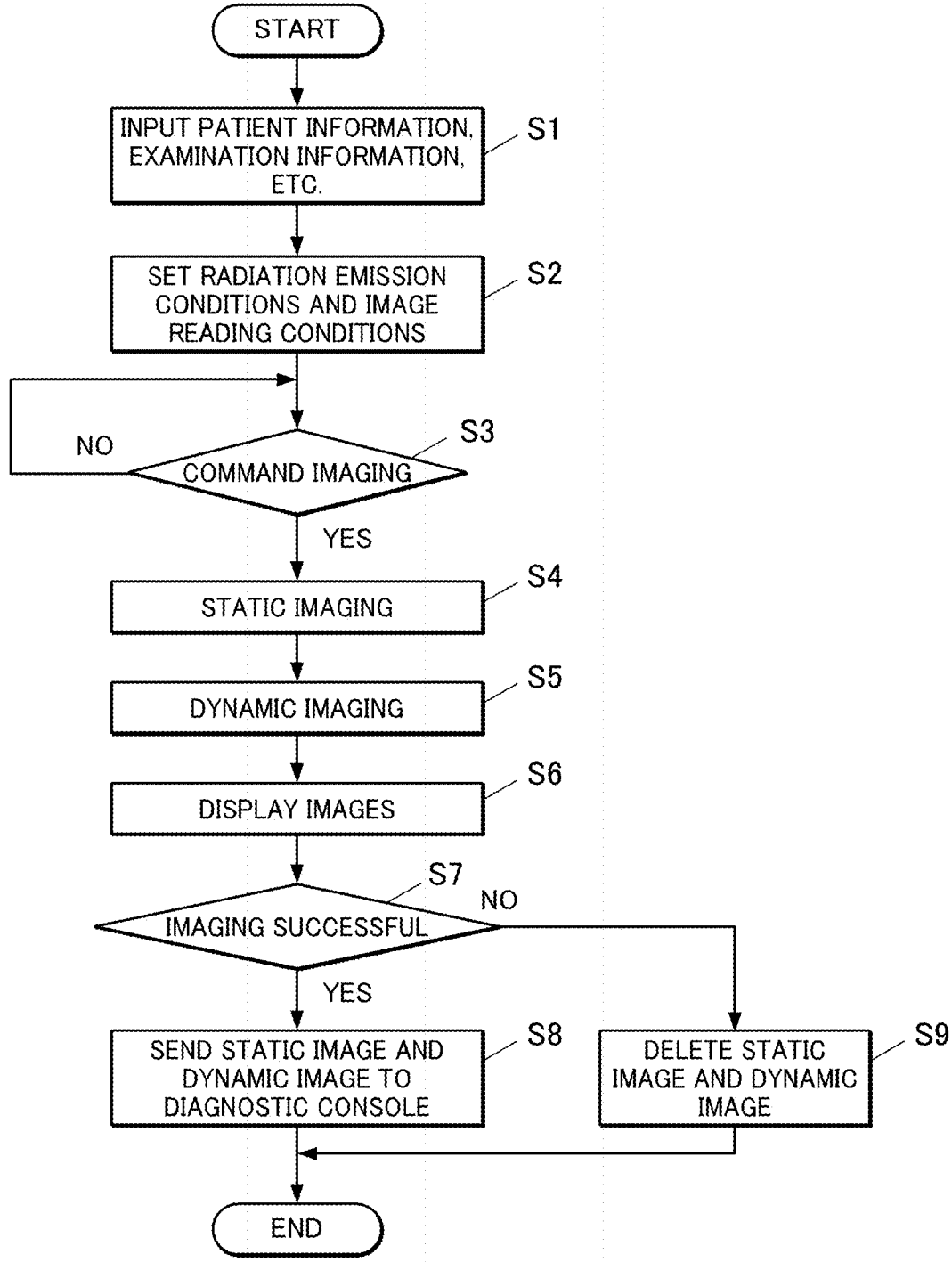
FIG. 3 is a flowchart showing an imaging control process executed on an imaging console.

FIG. 3 shows the imaging control process performed by the imaging console 2. The imaging control process is performed by the controller 21 in cooperation with the program(s) stored in the storage 22.

First, an examiner operates the operation interface 23 of the imaging console 2 to input patient information of the subject (M) and examination information (Step S1).

Next, the controller 21 reads radiation emission conditions from the storage 22 so as to set them in the radiation emission controller 12, and also reads image reading conditions from the storage 22 so as to set them in the reading controller 14 (Step S2).

Next, the controller 21 is on standby for an imaging command to be input via the operation interface 23 (Step S3). Here, the examiner places the subject M between the radiation source 11 and the radiation detector 13 for positioning. When imaging is ready, the examiner operates the operation interface 23 so as to input an imaging command.

In receipt of the imaging command input via the operation interface 23 (Step S3; YES), the controller 21 outputs an imaging command of a static image to the radiation emission controller 12 and the reading controller 14 and starts static imaging (Step S4). The static image obtained by imaging are input to the imaging console 2 and stored in the storage 22.

Next, the controller 21 outputs an imaging command of a dynamic image to the radiation emission controller 12 and the reading controller 14 and starts dynamic imaging (Step S5). Specifically, the radiation source 11 emits radiation at pulse intervals set in the radiation emission controller 12, and accordingly the radiation detector 13 obtains (generates) a series of frame images. When imaging of a predetermined number of frame images is done, the hardware processor 21 outputs an imaging end command to the radiation emission controller 12 and the reading controller 14 and stops the imaging actions. The frame images obtained by imaging are successively input to the imaging console 2 and stored in the storage 22, being associated with successive numbers indicating the imaging order of the respective frame images (frame numbers).

Next, the controller 21 displays the static image and the dynamic image on the display 24 (Step S6).

The examiner checks the static image and the dynamic image, and determines whether the images are suitable for diagnosis (imaging successful) or re-imaging is necessary (imaging unsuccessful). The examiner then operates the operation interface 23 to input the determination.

If the determination indicating "successful imaging" is input via the operation interface 23 (Step S7; YES), the controller 21 attaches, to the static image and the respective frame images obtained by dynamic imaging (e.g. writes in the header region of the image data in DICOM), information such as IDs to identify the images, the patient information, the examination information, the radiation emission conditions, the image reading conditions, and the like, and sends them to the diagnostic console 3 by the communication unit 25 (Step S8). The successive numbers indicating the imaging order of the respective frame images (frame numbers) are attached to the frame images of the dynamic image.

On contrary, if the determination indicating "unsuccessful imaging" is input via the operation interface 23 (Step S7; YES), the controller 21 deletes the static image and the dynamic image stored from the storage 22 (Step S9). In that case, re-imaging is required.

After Step S8 or S9, the imaging control process ends.

(Actions of Diagnostic Console)

Next, actions of the diagnostic console 3 are described.

Figure 4:
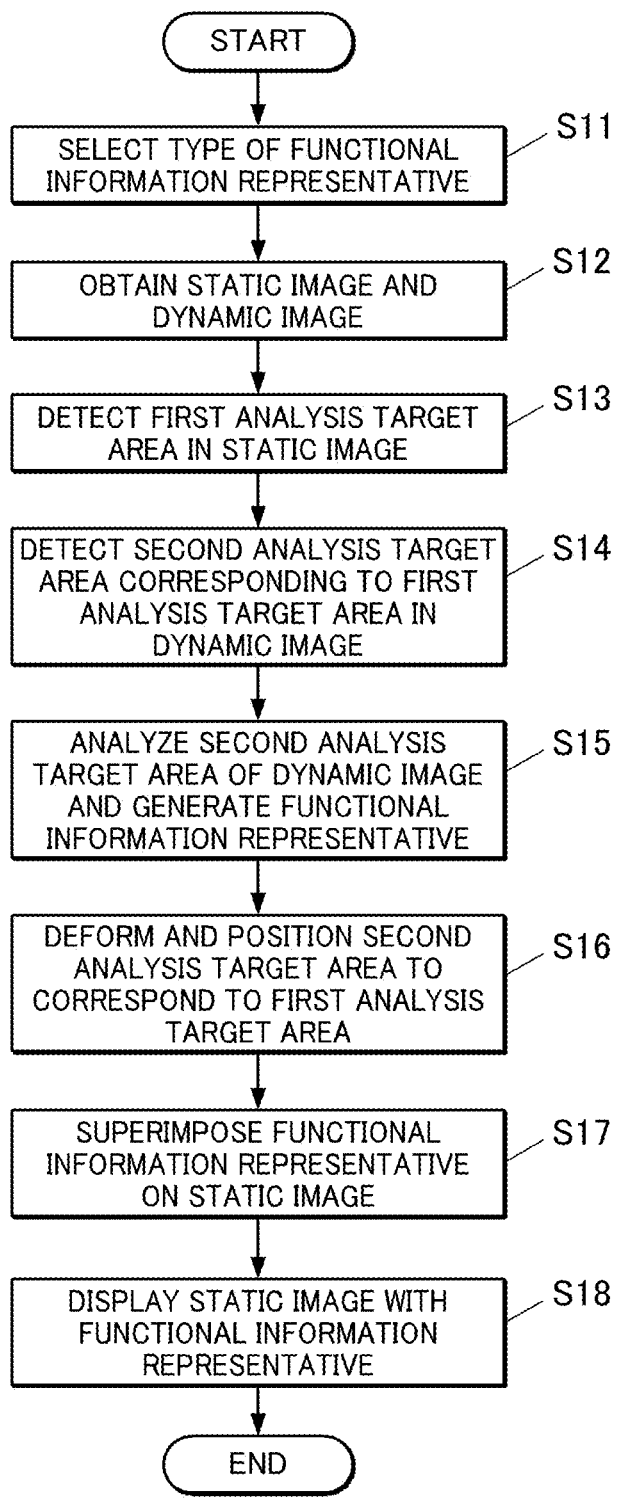
FIG. 4 is a flowchart showing a functional information representative addition process executed on a diagnostic console.

FIG. 4 shows a functional information representative addition process executed on the diagnostic console 3. The functional information representative addition process is executed by the controller 31 in cooperation with the program(s) stored in the storage 32.

First, on the diagnostic console 3, a type of the functional information representative to be displayed is selected with operation via the operation interface 33 by an image diagnostician such as a doctor (Step S11). For example, in a case where the functional information representative indicating ventilation is to be added on a static image, "ventilation" is selected. Multiple types of the functional information representative may be selected. The type of the functional information representative may be preset.

Next, the controller 31 obtains the static image and the dynamic image (a series of frame images) from the imaging console 2 via the communication unit 35 (Step S12), and the obtained static image and dynamic image are stored in the storage 32.

The controller 31 then detects the first analysis target area on the static image (Step S13). For example, the "lung field" is detected on a frontal chest image (static image). Specifically, a contour of the lung field is recognized by known image processing technologies of edge detection, dynamic contour model, segmentation, and the like.

The controller 31 then detects the second analysis target area corresponding to the first analysis target area on the dynamic image (Step S14). For example, the "lung field" is detected on a frontal chest image (each frame image of the dynamic image). Specifically, a contour of the lung field is recognized by known image processing technologies of edge detection, dynamic contour model, segmentation, and the like.

Next, the controller 31 analyzes the second analysis target area of the dynamic image and generates the functional information representative from the change caused by biological motion (Step S15).

For example, for ventilation, blood flow, a ventilation and blood flow balance, a lung motion amount, or lung movement directions, the controller 31 specifies a frame image (singular point) where change caused by the biological motion is the maximum as a singular point, and sets the functional information at the singular point as the functional information representative.

Alternatively, the controller 31 generates the functional information representative (a single representative image) by image processing of multiple images with pixel values indicating change caused by biological motion corresponding to each of multiple frame images of a dynamic image. The image processing includes maximum intensity projection processing, minimum intensity projection processing, and peak-to-peak processing.

For an abnormal site, the controller 31 detects an abnormal site in the functional information corresponding to each frame image of the dynamic image and generates an image indicating the abnormal site as the functional information representative.

For example, signal values indicating the functional information in the normal state (normal values) are stored as the reference values, and an area largely deviating from the normal values is specified as an abnormal site.

Figure 5:
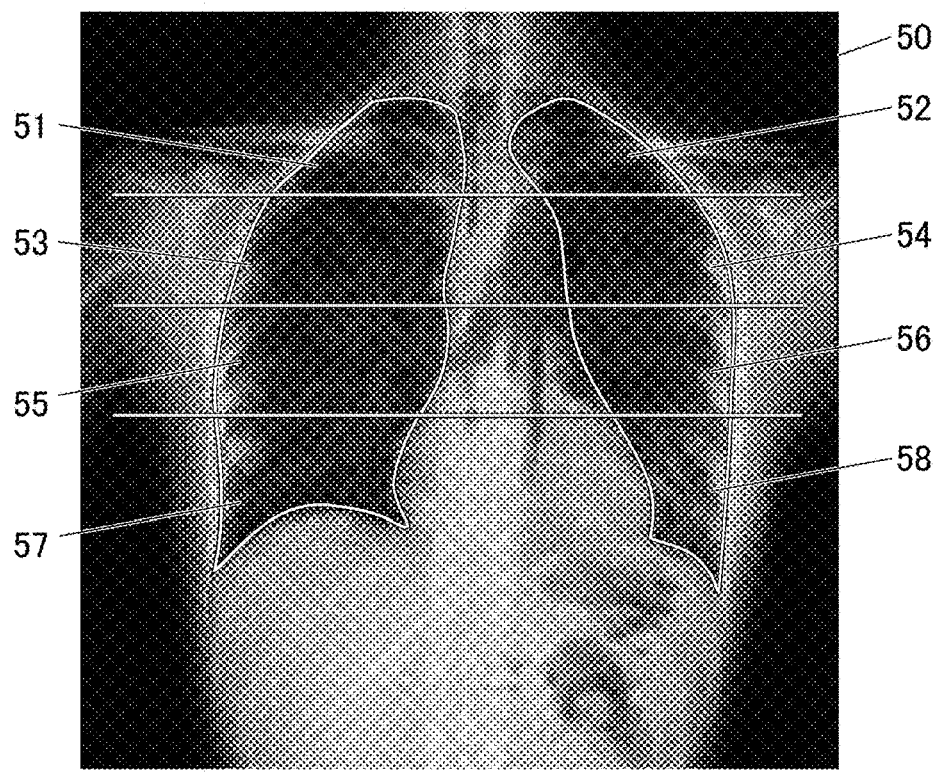
FIG. 5 is an explanatory drawing showing an exemplary method of detecting an abnormal site.

As shown in FIG. 5, an abnormal site may be detected by assigning ROIs 51 to 58 in the lung field on a frontal chest image 50, where the ROIs are aligned to the same height on the left and right. A difference between the average signal values indicating the functional information of the ROIs aligned to the same height on the left and right (for example, ROI 51 and ROI 52) is calculated, and a region with a large difference on one side is specified as an abnormal site.

For a thorax width, a respiratory tract diameter, a heart width, a lung field area, a respiratory tract area, or a heart area, the controller 31 specifies frame images where the measured values are the maximum and the minimum as singular points, and generates the functional information representative (the maximum and minimum measured values, lines, arrows, contours, or the like) from the functional information at the singular points.

For a diaphragm motion amount, the controller 31 specifies frame images where the diaphragm is at the highest and the lowest positions as singular points, and generates the functional information representative (lines or the like indicating the diaphragm motion amount or the diaphragm position) from a difference in the diaphragm position between those frame images (change amount).

Next, the controller 31 deforms and positions the second analysis target area so that the second analysis target area including the functional information representative corresponds to the first analysis target area (Step S16). For example, multiple pairs of corresponding points are obtained on the contours of the first analysis target area and the second analysis target area, and shift vectors between the corresponding points (motion amount vectors) are calculated. Then, an affine transformation is performed in the second analysis target area based on the shift vectors and thereby the second analysis target area corresponds to the first analysis target area.

Next, the controller 31 overlays the functional information representative in the deformed and positioned second analysis target area on the static image (Step S17). The functional information representative may be layered on the static image after the functional information representative is made transparent with a predetermined transparency.

The controller 31 then displays, on the display 34, the static image on which the functional information representative is overlaid (Step S18).

The functional information representative addition process ends here.

In a case where the functional information representative in the image group is selected, an image indicating the motion along with biological motion is added to the static image.

Figure 6:
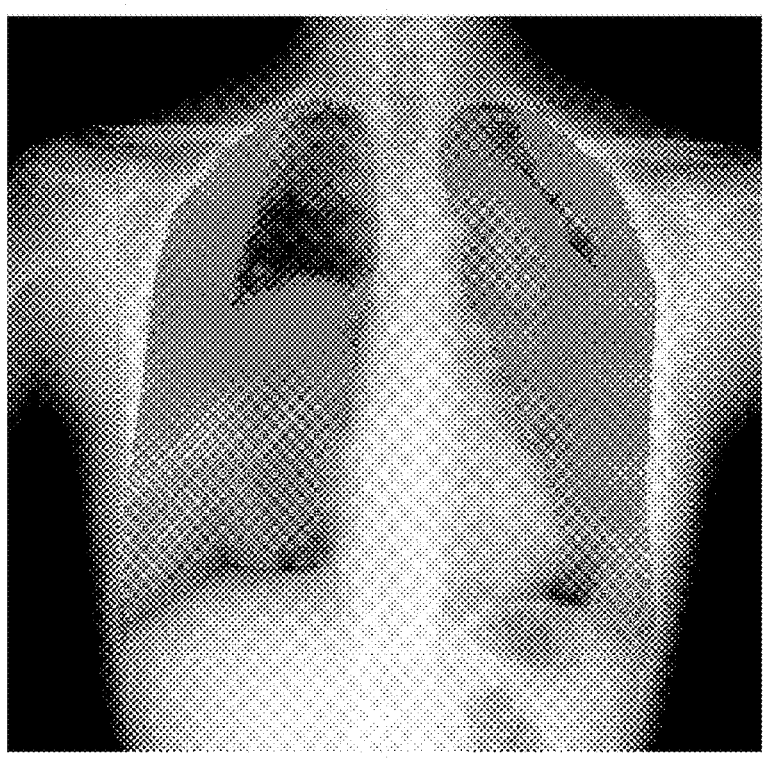
FIG. 6 shows an exemplary image where a functional information representative indicating a lung motion amount is overlaid on a frontal chest image.

FIG. 6 shows an exemplary image where the functional information representative indicating a lung motion amount is overlaid on a frontal chest image (static image). In FIG. 6, the functional information representative is visualized by coloring according to the lung motion amounts.

Figure 7:
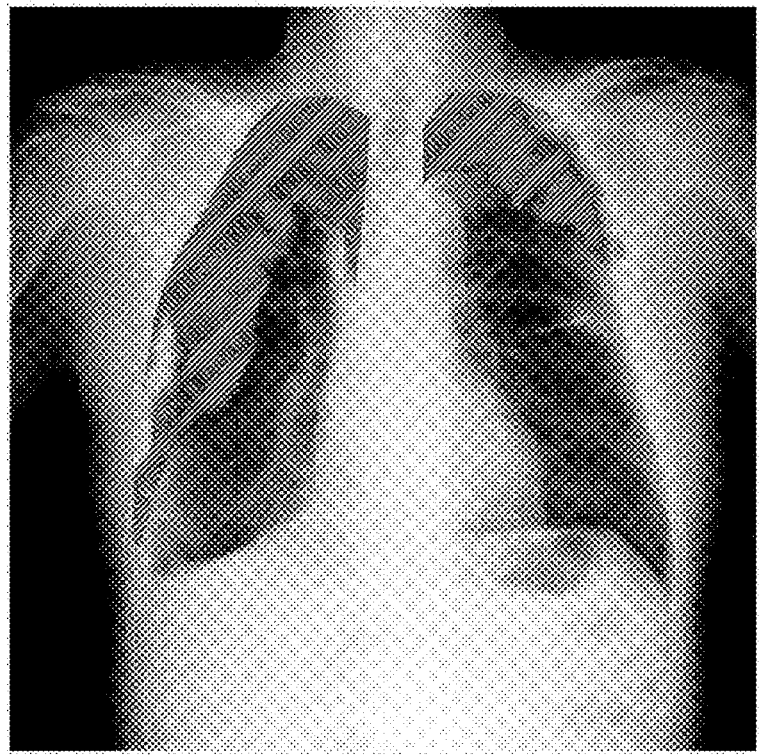
FIG. 7 shows an exemplary image where the functional information representative indicating an abnormal site obtained from a lung motion amount is overlaid on a frontal chest image.

FIG. 7 shows an exemplary image where the functional information representative indicating an abnormal site obtained from a lung motion amount is overlaid on a frontal chest image (static image). In FIG. 7, a position corresponding to an abnormal site as the functional information representative is visualized by predetermined coloring. In a case where the lung motion amount is locally decreased, a pleurodesis or emphysema may be present.

In a case where the functional information representative in the measurement group is selected, the measured values and measurement positions are added to the static image. As the measured values vary along with biological motion, a combination of the maximum value and the minimum value, the maximum change amount, or the like is displayed as the measured values.

Specifically, the measurement positions are displayed by lines and dots on the static image. In a case where a width or diameter is measured, the measured range is displayed by arrows and measured values.

Figure 8:
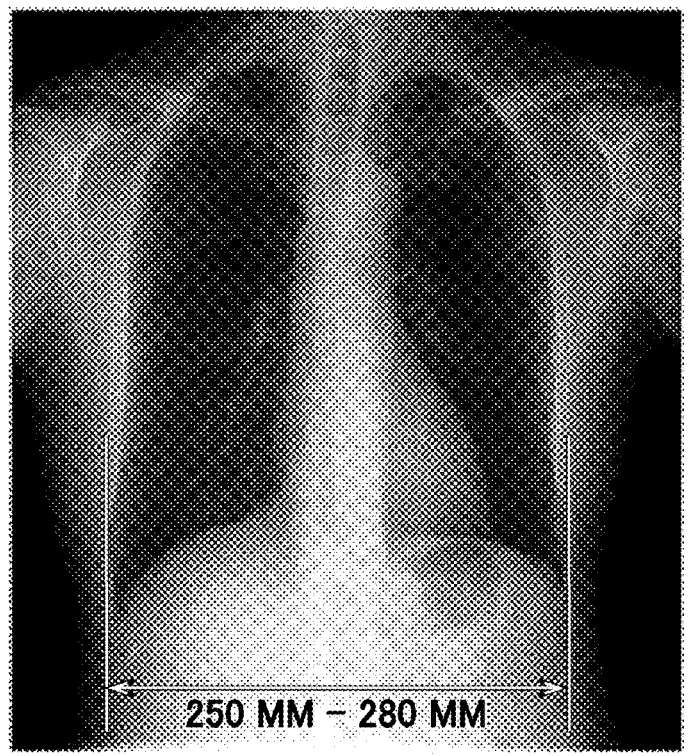
FIG. 8 shows an exemplary image where the functional information representative indicating a thorax width is overlaid on a frontal chest image.

FIG. 8 shows an exemplary image where the functional information representative indicating a thorax width is overlaid on a frontal chest image (static image). In FIG. 8, the maximum and minimum values of the thorax width and a line and arrows indicating and the position of the thorax width are shown as the functional information representative.

Figure 9:
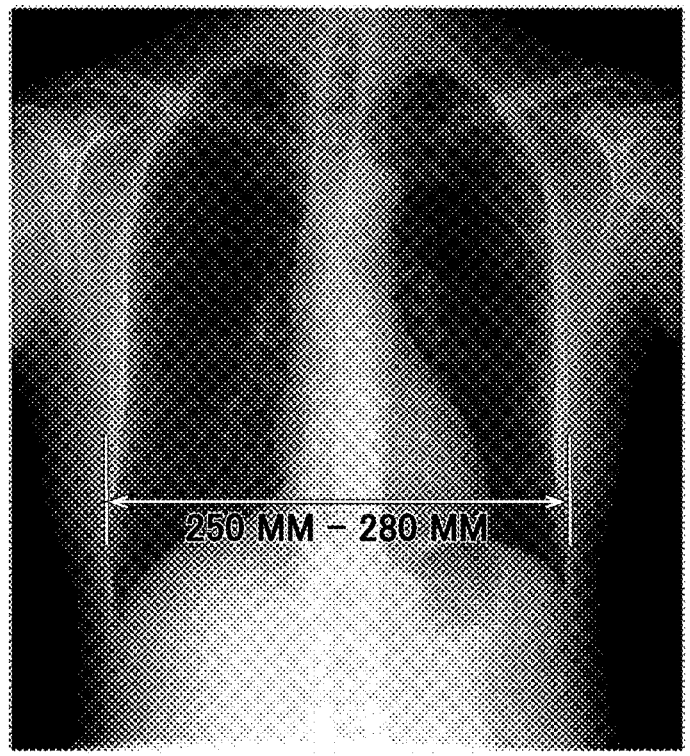
FIG. 9 shows an exemplary image where the functional information representative indicating a thorax width is overlapped with a frontal chest image.

The displayed arrows and the measured values are preferably positioned not to overlap with the analysis target area (region of interest). If the arrows and measured values indicating the thorax width overlap with the lung field on the frontal chest image as shown in FIG. 9, it may be a hindrance to diagnosis. Thus, the displayed arrows and the measured values are positioned not to overlap with the lung field on the frontal chest image as shown in FIG. 8.

For example, when the measured area is in the upper half of the image, the arrows and values are shown between the lung field area and the upper end of the image. When the measured area is in the lower half of the image, the arrows and values are shown between the lung field area and the lower end of the image.

In a case where an area is measured, the measured range is displayed by a contour and measured values.

Figure 10:
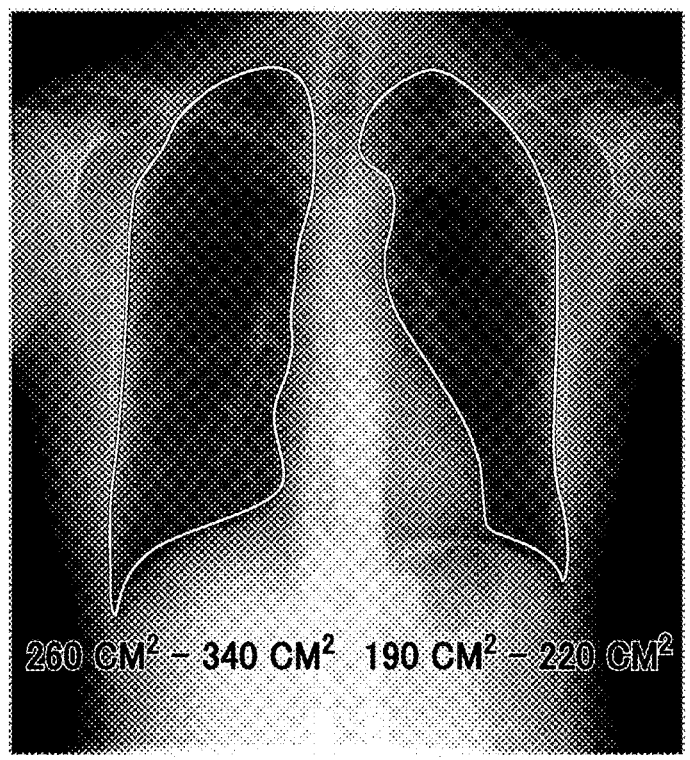
FIG. 10 shows an exemplary image where the functional information representative indicating a lung field area is overlaid on a frontal chest image.

FIG. 10 shows an exemplary image where the functional information representative indicating a lung field area is overlaid on a frontal chest image (static image). In FIG. 10, the minimum and maximum values of the lung field area calculated for left and right lungs and the contour of the lung field area on the left and right are shown as the functional information representative.

As described hereinbefore, according to this embodiment, a representative result (functional information representative) is generated from functional information obtained by analysis of a dynamic image and is overlaid on a static image, which makes it possible to read the functional information representative on a single image. This saves doctors time for diagnosis.

As the static image on which the representative functional image is overlaid is displayed, diagnostic evaluation for the dynamic image can be omitted.

In a case where the representative functional information is generated from a frame image where change caused by biological motion is the maximum among multiple frame images of a dynamic image, the functional information representative capturing a moment when the biological motion is largest may be generated.

In a case where a single representative image by image processing (maximum intensity projection processing, minimum intensity projection processing, peak-to-peak processing, or the like) of multiple images with pixel values indicating change caused by biological motion corresponding to each of multiple frame images of a dynamic image, a type of the image processing may be selected according to the object.

The above description of the embodiments is an example of the image processing apparatus and the image processing method according to the present invention, and is not intended to limit the scope of the invention. The detailed configurations/components and operations of the components constituting the image forming apparatus can also be appropriately modified within the scope of the present invention.

For example, a static image may not be taken separately from a dynamic image. Part of frame images of a dynamic image may be combined to generate a composite image as a static image. A composite image may also be generated from the average pixel values of frame images calculated for each pixel.

In a frontal chest image during respiration, the image densities vary according to the respiratory movement of exhalation and inhalation. A composite image may be generated by combining frame images in the same phase (or a near phase) in the respiratory movement among multiple frame images of a dynamic image, or frame images during the maximum inhalation (or exhalation) in the respiratory movement.

FIG. 11 shows changes in the average pixel values in the lung field along frames (time) of a dynamic image (frontal chest image). The part where the pixel values are small corresponds to exhalation, and the part where the pixel values are large corresponds to inhalation. The average pixel values vary according to the heartbeat in a period shorter than that of the respiration. A composite image may be generated by combining frame images of the maximum inhalation in the systolic phase corresponding to points P1 to P4 as shown in FIG. 11, and used as the static image.

In a case where a dynamic image (frontal chest image) is taken while the subject holds the breath, a composite image may be generated by combining multiple frames during the breath holding or combining frame images corresponding to a systolic (or diastolic) phase.

In the functional information representative addition process (see FIG. 4), the steps after Step S13 are performed after both a static image and a dynamic image are obtained (Step S12). However, any performable step may be started when either one of a static image and a dynamic image is obtained (Step S13 when a static image is obtained, and Steps S14 and S15 when a dynamic image is obtained).

In the above embodiment, the diagnostic console 3 executes the functional information representative addition process. However, the image management device (PACS) may store the functional information representative generated by the image processing apparatus such as the diagnostic console 3 and overlays the functional information representative on the static image in response to a command from a computer to obtain the image so that the static image with the functional information representative imposed is displayed on the display of the computer.

In a case where the measured values are displayed on the static image as the functional information representative, the positions of the lines and contour indicating the measured object may be obtained from the first analysis target area of the static image.

In the above description, a non-volatile semiconductor memory, a hard disk, and the like are used as the computer-readable medium storing the programs for executing the operations, but the present invention is not limited to these examples. A portable storage medium such as a CD-ROM can be used as the computer readable recording medium. A carrier wave may be also used as a medium providing the program data via a communication line.

What is claimed is:

1. An image processing device comprising a hardware processor,
   wherein the hardware processor:
   obtains a static image and a dynamic image of a same subject by radiographic imaging;
   detects, on the static image, a first analysis target area;
   detects, on the dynamic image, a second analysis target area corresponding to the first analysis target area;
   analyzes the second analysis target area of the dynamic image to generate a functional information representative from change caused by biological motion;
   deforms and positions the second analysis target area so that the second analysis target area corresponds to the first analysis target area;
   overlays the functional information representative of the deformed and positioned second analysis target area on the static image to generate a single final output image; and
   displays the single final output image on a display, and the functional information representative which is overlaid on the static image is placed at a position that is not covered by the first and second analysis target areas.

2. The image processing device according to claim 1, wherein the functional information representative indicates ventilation, blood flow, a ventilation and blood flow balance, a lung motion amount, or a lung movement direction.

3. The image processing device according to claim 2, wherein the hardware processor generates the functional information representative from a frame image where the change caused by the biological motion is a maximum among multiple frame images of the dynamic image.

4. The image processing device according to claim 2, wherein the hardware processor generates a representative image as the functional information representative by image processing on multiple images that include pixel values indicating the change caused by the biological motion, and that respectively correspond to multiple frame images of the dynamic image.

5. The image processing device according to claim 4, wherein the image processing is maximum intensity projection processing, minimum intensity projection processing, or peak-to-peak processing.

6. The image processing device according to claim 1, wherein the functional information representative indicates a measurement of thorax width, diaphragm motion amount, respiratory tract diameter, heart width, lung field area, respiratory tract area, or heart area.

7. The image processing device according to claim 1, wherein the functional information representative indicates an abnormal site.

8. The image processing device according to claim 1, wherein the static image is a composite image of part of multiple frame images of the dynamic image.

9. The image processing device according to claim 1, wherein the functional information representative which is overlaid on the static image varies in color according to a value or a position, or in size and position according to lines and arrows.

10. The image processing device according to claim 1, wherein the analysis target areas are lung fields.

11. An image processing method comprising:
   obtaining a static image and a dynamic image of a same subject by radiographic imaging;
   detecting, on the static image, a first analysis target area;
   detecting, on the dynamic image, a second analysis target area corresponding to the first analysis target area;
   analyzing the second analysis target area of the dynamic image to generate a functional information representative from change caused by biological motion;
   deforming and positioning the second analysis target area so that the second analysis target area corresponds to the first analysis target area;
   overlaying the functional information representative of the deformed and positioned second analysis target area on the static image to generate a single final output image; and
   displaying the single final output image on a display,
   wherein the functional information representative which is overlaid on the static image is placed at a position that is not covered by the first and second analysis target areas.

12. An image processing device comprising a hardware processor,
   wherein the hardware processor:
   obtains a static image and a dynamic image of a same subject by radiographic imaging;
   detects, on the static image, a first analysis target area;
   detects, on the dynamic image, a second analysis target area corresponding to the first analysis target area;
   analyzes the second analysis target area of the dynamic image to generate a functional information representative from change caused by biological motion;
   deforms and positions the second analysis target area so that the second analysis target area corresponds to the first analysis target area;
   overlays the functional information representative of the deformed and positioned second analysis target area on the static image to generate a single final output image; and
   displays the single final output image on a display, and
   the functional information representative indicates a measurement of thorax width, diaphragm motion amount, respiratory tract diameter, heart width, lung field area, respiratory tract area, or heart area.

13. The image processing device according to claim 12, wherein the hardware processor generates the functional information representative from a frame image where the change caused by the biological motion is a maximum among multiple frame images of the dynamic image.

14. The image processing device according to claim 12, wherein the static image is a composite image of part of multiple frame images of the dynamic image.

15. The image processing device according to claim 12, wherein the functional information representative which is overlaid on the static image varies in color according to a value or a position, or in size and position according to lines and arrows.

* * * * *